United States Patent [19]

Calas et al.

[11] 4,451,682

[45] May 29, 1984

[54] PROCESS FOR THE PREPARATION OF TRUE ACETYLENE HYDROCARBONS HAVING A PERFLUORINATED CHAIN

[75] Inventors: Patrick Calas, Montpellier; Patrice Moreau, Saint Gely Du Fesc; Auguste Commeyras, Clapiers, all of France

[73] Assignee: PCUK Produits Chimiques Ugine Kuhlmann, Courbevoie, France

[21] Appl. No.: 446,387

[22] Filed: Dec. 2, 1982

[30] Foreign Application Priority Data

Dec. 29, 1981 [FR] France .................. 81 24364

[51] Int. Cl.³ ............................................ C07C 17/33
[52] U.S. Cl. ................................................ 570/142
[58] Field of Search ........................................ 570/142

[56] References Cited

U.S. PATENT DOCUMENTS

Re. 31,330  8/1983  Fujita et al. ........................ 570/142

Primary Examiner—Charles F. Warren
Assistant Examiner—Joseph A. Boska
Attorney, Agent, or Firm—Pennie & Edmonds

[57] ABSTRACT

Process for the preparation of true acetylene hydrocarbons with a perfluoro chain, characterized by dehydroiodination with an alkali metal hydroxde in an alcoholic medium of the iodohydrin

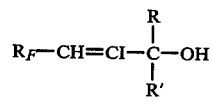

wherein $R_F$ is a straight or branched perfluoroalkyl chain $C_nF_{2n+1}-$ where n is 1 to 20, and R and R' are identical or different alkyl radicals, followed by distillation, in the presence of solid alkali metal hydroxide, of the resulting acetylenic alcohol obtained to produce a true acetylene hydrocarbon of the formula $R_F-C\equiv CH$. The acetylene hydrocarbons are useful for forming compounds having the ability to carry gases such as oxygen for biological purposes.

4 Claims, 1 Drawing Figure

U.S. Patent     May 29, 1984     4,451,682
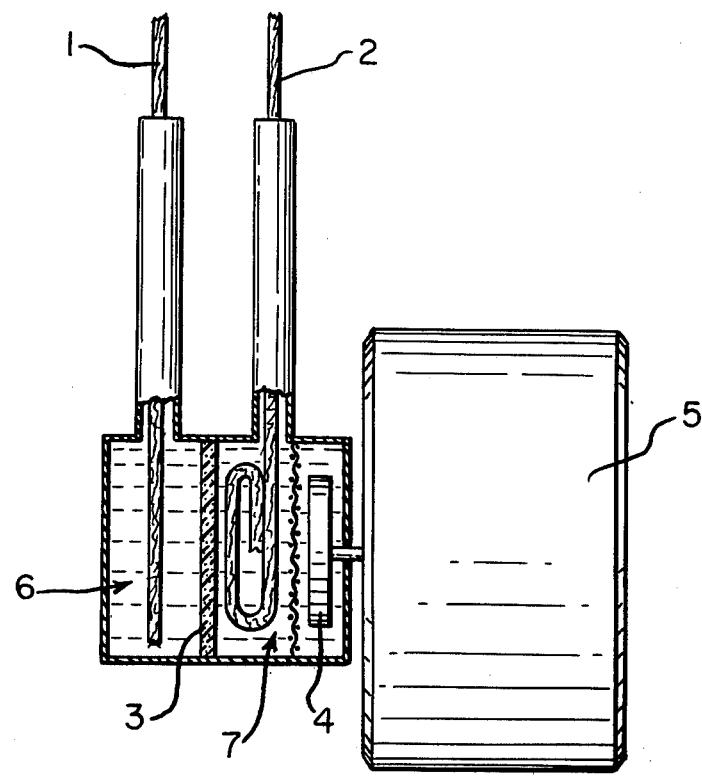

PROCESS FOR THE PREPARATION OF TRUE ACETYLENE HYDROCARBONS HAVING A PERFLUORINATED CHAIN

TECHNICAL FIELD

This invention relates to a process for the preparation of acetylene hydrocarbons with a perfluoro chain of general formula $R_F\text{—}C\equiv CH$ which are referred to as true acetylene hydrocarbons, wherein $R_F$ denotes a straight chain or branched perfluoroalkyl radical $C_nF_{2n+1}\text{—}$. These compounds are useful as intermediates for introducing perfluoroalkyl chains into organic molecules to produce end products useful as solvents for gases such as oxygen.

BACKGROUND OF THE INVENTION

The products $C_nF_{2n+1}\text{—}C\equiv CH$ wherein n is 1, 2 or 3 (namely $CF_3$, $C_2F_5$ or $C_3F_7$) are known from the articles by A. L. Henne and M. Nager, J. AMER. CHEM. SOC. 1951, 73, 1042 and by R. N. Haszeldine and K. Leedham, J. CHEM. SOC. 1952, 3483. Compounds with a longer perfluoroalkyl chain have been prepared more recently by successive reactions of bromination, dehydrobromination and debromination, for example, by M. LeBlanc et al., J. FLUORINE CHEM. 1976, 7, 525, or by a reaction initiated by couplings based on copper between perfluoroalkyl iodides, $R_FI$, and unsaturated substrates, as described in J. ORG. CHEM. 1975, 40, 810, but these processes require numerous steps which result in poor yields.

SUMMARY OF THE INVENTION

The applicants have perfected a process for preparing true acetylene hydrocarbons with a perfluoro chain with excellent yields, starting from products which are easy to obtain. This process consists in reacting a perfluoroalkyl iodide with a tertiary acetylenic alcohol to form an iodohydrin and then, after the resulting iodohydrin has been dehydroiodinated to form the corresponding perfluorinated acetylenic alcohol, distillation of the perfluorinated acetylenic alcohol over solid sodium hydroxide results in a mixture of the perfluorinated true acetylene hydrocarbon and a ketone.

BRIEF DESCRIPTION OF THE DRAWING

The single drawing FIGURE of this application is a schematic illustration of the apparatus which can be used to carry out the process of the present invention.

DETAILED DESCRIPTION OF THE INVENTION

The various reactions carried out according to this invention are as follows:

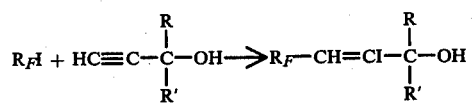

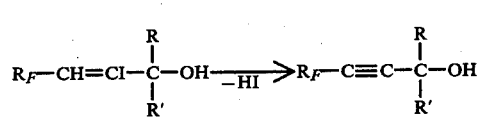

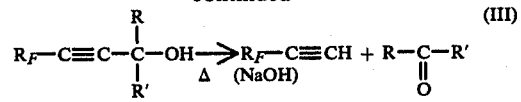

R and R' represent identical or different alkyl radicals and $R_F$ is the radical $C_nF_{2n+1}\text{—}$ where n is 1 to 20.

The molar ratio of $R_FI$ to acetylenic alcohol may vary from between about 3/1 and 1/5. For reaction II, the molar ratio of iodohydrin to KOH can vary from between about 1/1 and 1/5. For both these reactions, the temperature may be from 20° to 100° C. The distillation during which reaction III takes place is carried out at elevated temperature or the distillation temperature of the acetylenic alcohol.

In the case under consideration, wherein R and R' are alkyl radicals, the iodohydrin obtained is in the trans form, the only form which can lead to the product of reaction (II). Product of reaction II can be produced either directly in the electrolysis cell, allowing the pH of the cathode to rise, or, preferably, by treating it with potassium hydroxide in an alcoholic medium, with a yield of the order of 95%. The perfluorinated acetylene is obtained by distillation of product II over solid sodium hydroxide while the ketone which is a by-product is separated off during the distillation.

R and R' can be the same or different alkyl radicals and can be straight chain or branched radicals. The number of carbon atoms contained in these radicals should not adversely affect or interfere with the reactions I, II and III. The by-product ketone produced, which is determined by the alkyl radicals employed, also plays a part in the selection of the alkyl group. It is thus advantageous to select lower alkyl groups (1 to 6 carbon atoms) for R and R'. R and R' are thus preferably methyl or mixed methyl and ethyl producing acetone or methyl ethyl ketone respectively as by-products.

Most any alkali metal hydroxide can be used in reactions II and III. Sodium and potassium are of course preferred. It is also preferred to use potassium hydroxide in reaction II and sodium hydroxide in reaction III. The alcohol used in reaction II is preferably methanol but other alcohols can of course be used.

The following Examples illustrate the invention without limiting it.

EXAMPLE 1

A glass cell with two compartments 6 and 7 is used, as shown in the accompanying drawing.

Each compartment is a cylinder with a horizontal axis, 5 cm in diameter and 5 cm high and with a volume of 100 ml. The two compartments are separated by a sintered glass 3, 5 cm in diameter, having a porosity of 3.

The cathode compartment 7 contains a cathode 2 consisting of 60 cm of carbon fiber wick containing 10,000 fibers, 3μ thick per wick, such as, for example, RIGILOR AGTF 10,000, registered trademark of Messrs. Carbone-Lorraine, connected to the internal circuit by non-immersed copper wires (not shown). This compartment also contains an agitating bar magnet 4 placed in a vertical plane and separated from the carbon fibers by a nylon mesh with a mesh size of 2 mm. This bar is driven by an agitator 5.

The anode compartment 6 contains a carbon anode 1 consisting of a vertical bar 6 mm in diameter and the two electrodes are connected as in conventional electrolysis equipment.

100 g of $C_6F_{13}I$ mixed with 18.8 g of $HC\equiv C—C(CH_3)_2OH$ (molar ratio 1:1) and 30 ml of water saturated with KCl are placed in the cathode compartment. 100 ml of water saturated with KCl are placed in the anode compartment.

The electrolysis is effected under a set amperage of 0.7 amps. The ohmic drop in the cell is of the order of 11 volts.

After two hours, the electrolysis is stopped, the catholyte is drawn off and washed three times with 200 ml of water. The heavy organic phase is separated by decanting. Analysis of this phase reveals the presence of 80 g of trans iodohydrin $C_6F_{13}—CH=CI—C(CH_3)_2OH$, 30 g of unconverted $C_6F_{13}I$ and traces of acetylenic alcohol, $C_6F_{13}—C\equiv C—C(CH_3)_2—OH$. The iodohydrin yield, compared with the starting perfluoroalkyl iodide converted, is 98%.

The iodohydrin is purified by distillation in vacuo.

The faradic yield of the electrolysis is 0.3 farads per mole of $C_6F_{13}I$ converted.

7.6 g of potassium hydroxide (KOH) are added to 50 g of the iodohydrin obtained, dissolved in 200 ml of methanol, which corresponds to a molar ratio of KOH to iodohydrin of 1 to 5. The mixture is left for two hours at ambient temperature, then washed three times with 500 ml of water. A colorless layer of 37.9 g separates off, consisting of the acetylene, $C_6F_{13}—C\equiv C—(CH_3)_2OH$, which constitutes a quantitative yield.

10 g of this acetylene alcohol and 3 pellets of sodium hydroxide (NaOH) are placed in a 25 ml Claisen flask. The mixture is distilled slowly and a product is obtained which distils over at 95° C.; heating is continued until vapors pass over at 180° C.

The receiving flask contains an equimolar mixture of acetone and 5.6 g of acetylene $C_6F_{13}—C\equiv CH$ which are separated by distillation. A yield of 65% for the cutoff reaction is obtained.

EXAMPLES 2 TO 4

The same procedure is used as in Example 1, but with products having different $R_F$, R and R' radicals. The following Table shows the results obtained.

| Starting products | | | Perfluorinated acetylene | |
|---|---|---|---|---|
| $R_F$ | R | R' | Boiling point (°C.) | Yield from distilliation |
| $C_4F_9$ | $CH_3$ | $CH_3$ | 42 | 80 |
| $C_4F_9$ | $CH_3$ | $C_2H_5$ | 42 | 65 |
| $C_6F_{13}$ | $CH_3$ | $C_2H_5$ | 94–96 | 70 |

EXAMPLE 5

0.1 mole (8.4 g) of the alcohol $HC\equiv C—C(CH_3)_2OH$, 5 ml of dimethyl formamide (DMF), $1.5\times10^{-3}$ mole (0.98 g) of $Hg_2I_2$, $6\times10^{-3}$ mole (2.72 g) of $HgI_2$ and 0.02 mole (8.92 g) of $C_6F_{13}I$ are placed in a 250 ml reactor fitted with a magnetic stirrer. The mixture is heated to 35°–40° C. for 72 hours. After this time, all the $C_6F_{13}I$ is converted. The yield of iodohydrin, checked by gas chromatography and NMR ($H^1$ and $F^{19}$) is quantitative. The product is separated off by pouring the reaction mixture into 250 ml of water. A dense layer forms, which is separated and extracted with $CCl_4$. After drying and evaporation of the $CCl_4$, 9.2 g of the iodohydrin, $C_6F_{13}—CH=CI—C(CH_3)_2OH$, are obtained (yield 86.8%) which may be used in the remaining reactions described in Example 1, to give the corresponding true acetylene, $C_6F_{13}—C\equiv CH$.

The true acetylene hydrocarbons are useful for the production of compounds of longer perfluoroalkyl chains which are of low toxicity and are good solvents for gases such as oxygen. An example of such a use would involve the production of $$R_F—CH=C—C=CH—R_F \quad\quad (IV)$$
$$\phantom{R_F—CH=}\overset{|}{R_F}\;\overset{|}{R_F}$$

by the following reaction sequence:

$$R_FI + R_FC\equiv CH \xrightarrow[3h]{220°\ C.} R_FCH=CIR_F + R_F(CH=C—)_2I$$
$$\phantom{xxxxxxxxxxxxxxxxxxxxxxxxxxxxxxxxxxxxxxxxxxxxx}\overset{|}{R_F}$$

$$R_FCH=CIR_F \xrightarrow[220°\ C./4h]{Cu} R_F—CH=C—C=CHR_F\ (IV) +$$
$$\phantom{xxxxxxxxxxxxxxxxxxxxxxxxxxxxxxxxxxxxx}\overset{|}{R_F}\ \overset{|}{R_F}$$

$$R_F—CH=CH—R_F$$

where $R_F$ has the same meaning as defined above.

The highly fluorinated compound IV is inert, of low toxicity and useful as an inert oxygen carrier for biological purposes, for example, artificial blood. See Tetrahedron Vol. 30 (1974) 4197 which is incorporated herein by reference.

We claim:

1. Process for the preparation of true acetylene hydrocarbons with a perfluoroalkyl chain comprising dehydroiodinating the trans iodohydrin $$R_F—CH=CI—\overset{\overset{\displaystyle R}{|}}{\underset{\underset{\displaystyle R'}{|}}{C}}—OH$$

wherein $R_F$ is a straight or branched perfluoroalkyl chain, $C_nF_{2n+1}—$, n is 1 to 20, and R and R' are identical or different alkyl radicals in the presence of alkali metal hydroxide in an alcohol medium to obtain the corresponding acetylenic alcohol, and distillating the acetylenic alcohol in the presence of solid alkali metal hydroxide to obtain $R_FC\equiv CH$.

2. The process according to claim 1 in which the alkali metal hydroxide used in the dehydroiodinating step is potassium hydroxide and the alkali metal used in the distillation step is sodium hydroxide.

3. The process of claim 2 in which the alkyl radicals contain 1 to 6 carbon atoms.

4. The process of claim 1 in which the alkyl radicals contain 1 to 6 carbon atoms.

* * * * *